US010590204B2

(12) United States Patent
Katinger et al.

(10) Patent No.: US 10,590,204 B2
(45) Date of Patent: *Mar. 17, 2020

(54) RECOMBINANT HUMAN IGM-ANTIBODY EFFECTIVE AGAINST CANCER CELLS

(71) Applicant: Katinger GmbH, Vienna (AT)

(72) Inventors: Hermann Katinger, Vienna (AT); Renate Kunert, Deutsch-Wagram (AT); Thomas Sterovsky, Nodendorf (AT); Thomas Hemetsberger, Klosterneuburg (AT)

(73) Assignee: KATINGER GMBH (AT)

(*) Notice: Subject to any disclaimer, the term of this patent is extended or adjusted under 35 U.S.C. 154(b) by 0 days.

This patent is subject to a terminal disclaimer.

(21) Appl. No.: 15/891,466

(22) Filed: Feb. 8, 2018

(65) Prior Publication Data

US 2018/0237538 A1    Aug. 23, 2018

Related U.S. Application Data

(63) Continuation of application No. 14/646,166, filed as application No. PCT/EP2013/074762 on Nov. 26, 2013, now Pat. No. 9,920,130.

(60) Provisional application No. 61/731,586, filed on Nov. 30, 2012.

(51) Int. Cl.
*C07K 16/30* (2006.01)
*G01N 33/577* (2006.01)

(52) U.S. Cl.
CPC ...... *C07K 16/3084* (2013.01); *C07K 16/3015* (2013.01); *C07K 16/3023* (2013.01); *C07K 16/3053* (2013.01); *G01N 33/577* (2013.01); *C07K 2317/14* (2013.01); *C07K 2317/30* (2013.01); *C07K 2317/33* (2013.01); *C07K 2317/52* (2013.01); *C07K 2317/56* (2013.01); *C07K 2317/73* (2013.01); *C07K 2317/734* (2013.01); *G01N 2800/7028* (2013.01)

(58) Field of Classification Search
None
See application file for complete search history.

(56) References Cited

U.S. PATENT DOCUMENTS

| | | | |
|---|---|---|---|
| 5,006,470 A | 4/1991 | Yamaguchi et al. | 424/85.8 |
| 5,610,280 A * | 3/1997 | Brandt | C07K 16/3053 435/70.21 |
| 5,714,350 A | 2/1998 | Co et al. | |
| 6,933,368 B2 | 8/2005 | Co et al. | |
| 2007/0154469 A1* | 7/2007 | Irie | C07K 16/00 424/133.1 |

FOREIGN PATENT DOCUMENTS

| | | |
|---|---|---|
| EP | 0 480 440 A1 | 4/1992 |
| WO | WO 94/19457 A1 | 9/1994 |
| WO | WO 2010/002822 A1 | 1/2010 |

OTHER PUBLICATIONS

Azuma et al. Recombinant Human Hexamer-Dominant IgM Monoclonal Antibody to Ganglioside GM3 for Treatment of Melanoma. Clin Cancer Res 2007;13(9): 2745-2750.*
International Search Report dated Feb. 6, 2014 in corresponding PCT International Application No. PCT/EP2013/074762.
P. Fredman et al., "Gangliosides as Therapeutic Targets for Cancer," Biodrugs: Clinical Immunotherapeutics, Biopharmaceuticals and Gene Therapy, ADIS International, FR, 17(3):155-167, Jan. 1, 2003.
R.F. Irie et al., "Phase I pilot clinical trial of human IgM monoclonal antibody to ganglioside GM3 in patients with metastatic melanoma," Cancer Immunology and Immunotherapy, 53:110-1117, Jan. 1, 2004.
R.F. Irie et al., "Regression of cutaneous metastatic melanoma by intralesional injection with human monoclonal antibody to ganglioside GD2," Proceedings of the National Academy of Sciences USA, 83(22):8694-8698, Nov. 1, 1986.
M. Alfonso et al., "Generation of Human Monoclonal Antibodies Against Ganglioside Antigens and their Applications in the Diagnosis and Therapy of Cancer," Acta Oncologica 35(3):287-295, Jan. 1, 1996.
H. Hildebrandt, "Antigen binding of antiganglioside antibodies in vitro is strongly influenced by the ganglioside composition of the sample," FEBS Letters, 388(1):29-33, Jun. 1, 1996.
H.P. Vollmers, "Natural antibodies and cancer," New Biotechnology, 25(5):294-298, Jun. 2009.
S. Wolbank et al., "Characterization of Human Class-Switched Polymeric (Immunoglobulin M [IgM] and IgA) Anti-Human Immunodeficiency Virus Type 1 Antibodies 2F5 and 2G12," Journal of Virology, 77(7):4095-4103, Apr. 2003.
K. Vorauer-Uhl et al., "IgM characterization directly performed in crude culture supernatants by a new simple electrophoretic method," Journal of Immunological Method, 359:21-27, 2010.
Kuroda, Daisuke, et al. "Computer-aided antibody design." Protein engineering, design & selection 25.10 (2012):507-522.
Tiller, Kathryn E., and Peter M. Tessier. "Advances in antibody design." Annual review of biomedical engineering 17 (2015): 191-216.
Yu, Chung-Ming, et al. "Rationalization and design of the complementarity determining region sequences in an antibody-antigen recognition interface." PLoS One 7.3 (2012): e33340.
Pantazes, Robert J., and Costas D. Maranas. "MAPs: a database of modular antibody parts for predicting tertiary structures and designing affinity matured antibodies." BMC bioinformatics 14.1 (2013): 168.

(Continued)

Primary Examiner — Nianxiang Zou
(74) Attorney, Agent, or Firm — Ostrolenk Faber LLP

(57) ABSTRACT

A recombinant human monoclonal pentameric IgM antibody comprising the capability of oligospecific binding to purified ganglioside epitopes GD3, GM3, GD2 and GM1 and the capability of specific binding to malignant cancer cells selected from the group consisting of melanoma cells, small cell lung cancer cells, glioblastoma cells, and estrogen receptor-negative metastatic breast cancer cells; a cell line producing the IgM antibody; and the use of the IgM antibody as a diagnostic tool and/or as a therapeutic agent.

9 Claims, 7 Drawing Sheets

Specification includes a Sequence Listing.

(56) References Cited

OTHER PUBLICATIONS

Wright, Ann, and Sherie L. Morrison. "Effect of C2-associated carbohydrate structure on Ig effector function: studies with chimeric mouse-human IgG1 antibodies in glycosylation mutants of Chinese hamster ovary cells." The Journal of Immunology 160, No. 7 (1998): 3393-3402.

Wallick, S.C., Kabat, E.A. and Morrison, S.L., 1988. Glycosylation of a VH residue of a monoclonal antibody against alpha (1----6) dextran increases its affinity for antigen. Journal of Experimental Medicine, 168(3), pp. 1099-1109.

Sabouri, Zahra, Peter Schofield, Keisuke Horikawa, Emily Spierings, David Kipling, Katrina L. Randall, David Langley et al. "Redemption of autoantibodies on anergic B cells by variable-region glycosylation and mutation away from self-reactivity." Proceedings of the National Academy of Sciences 111, No. 25 (2014): E2567-E2575.

Beck, Alain, Elsa Wagner-Rousset, Marie-Claire Bussat, Maryline Lokteff, Christine Klinguer-Hamour, Jean-Fran ois Haeuw, Liliane Goetsch, Thierry Wurch, Alain V. Dorsselaer, and Nathalie Corva a. "Trends in glycosylation, glycoanalysis and glycoengineering of therapeutic antibodies and Fc-fusion proteins." Current pharmaceutical biotechnology 9, No. 6 (2008): 482-501.

Shade, Kai-Ting C., and Robert M. Anthony. "Antibody glycosylation and inflammation." Antibodies 2, No. 3 (2013):392-414.

Raju, S. "Glycosylation variations with expression systems." BioProcess International 1 (2003): 44-53.

Lifely, M. Robert, Christine Hale, Susan Boyce, Michael J. Keen, and Jenny Phillips. "Glycosylation and biological activity of CAMPATH-1H expressed in different cell lines and grown under different culture conditions." Glycobiology 5, No. 8 (1995): 813-822.

Rudd, Pauline M., and Raymond A. Dwek. "Glycosylation: heterogeneity and the 3D structure of proteins." Critical reviews in biochemistry and molecular biology 32, No. 1 (1997): 1-100. EFS Web 2.1.

\* cited by examiner

SEQUENCE LISTING

```
<160> NUMBER OF SEQ ID NOS: 2

<210> SEQ ID NO 1
<211> LENGTH: 126
<212> TYPE: PRT
<213> ORGANISM: Artificial Sequence
<220> FEATURE:
<223> OTHER INFORMATION: Heavy chain variable region of mature IgM
      protein PolrecCHOIgM/GD3
<220> FEATURE:
<221> NAME/KEY: PEPTIDE
<222> LOCATION: (1)..(126)
<223> OTHER INFORMATION: Heavy chain variable region of mature IgM
      protein PolrecCHO-IgM/GD3

<400> SEQUENCE: 1

Gln Val Gln Leu Val Gln Ser Gly Ala Glu Met Lys Lys Pro Gly Ala
1               5                   10                  15

Ser Val Lys Val Ser Cys Lys Ala Ser Gly Tyr Thr Phe Ser Ser Phe
            20                  25                  30

Ala Met His Trp Val Arg Gln Ala Pro Gly Gln Arg Leu Glu Trp Met
        35                  40                  45

Gly Trp Ile Asn Ala Gly Asn Gly Asn Thr Lys Tyr Ser Gln Lys Phe
    50                  55                  60

Gln Gly Arg Leu Thr Ile Thr Arg Asp Thr Ser Ala Ser Thr Ala Tyr
65                  70                  75                  80

Met Asp Leu Ser Ser Leu Arg Ser Glu Asp Thr Ala Val Tyr Tyr Cys
            85                  90                  95

Ala Arg Asn Leu Asn Tyr Tyr Asp Ile Leu Thr Gly Leu Asp Ala Phe
            100                 105                 110

Asp Ile Trp Gly Gln Gly Thr Met Val Thr Val Ser Ser Gly
            115                 120                 125

<210> SEQ ID NO 2
<211> LENGTH: 113
<212> TYPE: PRT
<213> ORGANISM: Artificial Sequence
<220> FEATURE:
<223> OTHER INFORMATION: Light chain variable region of mature IgM-
      protein PolrecCHOIgM/GD3
<220> FEATURE:
<221> NAME/KEY: PEPTIDE
<222> LOCATION: (1)..(113)
<220> FEATURE:
<221> NAME/KEY: PEPTIDE
<222> LOCATION: (1)..(113)
<223> OTHER INFORMATION: Light chain variable region of mature IgM
      protein PolrecCHOIgM/GD3

<400> SEQUENCE: 2

Asp Ile Val Met Thr Gln Ser Pro Asp Ser Leu Ala Val Ser Leu Gly
```

```
1               5                   10                  15
Glu Arg Ala Thr Ile Asn Cys Lys Ser Ser Gln Ser Val Leu Tyr Ser
            20                  25              30

Ser Asn Lys Lys Asn Tyr Leu Ala Trp Tyr Gln Gln Lys Pro Gly Gln
        35              40              45

Pro Pro Lys Leu Leu Ile Tyr Trp Ala Ser Thr Arg Glu Ser Gly Val
    50              55              60

Pro Asp Arg Phe Thr Gly Ser Gly Ser Gly Thr Asp Phe Thr Leu Thr
65              70              75              80

Ile Ser Ser Leu Gln Ala Glu Asp Val Ala Val Tyr Tyr Cys Gln Gln
            85              90              95

Tyr Tyr Ser Thr Pro Leu Thr Phe Gly Pro Gly Thr Lys Val Asp Ile
            100             105             110

Lys
```

RECOMBINANT HUMAN IGM-ANTIBODY EFFECTIVE AGAINST CANCER CELLS

CROSS-REFERENCE TO RELATED APPLICATIONS

The present application is a continuation of U.S. patent application Ser. No. 14/646,166, filed May 20, 2015, which is a 35 U.S.C. national phase conversion of PCT/EP2013/074762, filed Nov. 26, 2013, which claims priority to U.S. Provisional Patent Application No. 61/731,586, filed Nov. 30, 2012, the contents of which are incorporated herein by reference. The PCT International Application was published in the English language.

TECHNICAL FIELD

The present invention relates to the manufacture and use of IgM antibodies having a binding specificity for a number of gangliosides and being effective against various malignant tumor cells and cancers.

STATE OF THE ART

Gangliosides are complex glycolipid constituents of cell membranes. They are involved in many biological functions including cell-cell recognition, cell-matrix attachment, cell growth and cell differentiation. They are synthesized in the Golgi apparatus of the cell as a consequence of multienzyme pathways leading to different substructures. Studies of ganglioside expression in different "malignant cells" such as small cell lung cancer cells, melanomas, neuroblastomas, certain breast cancer cells and others reveal deviations of ganglioside expression as compared to "normal tissues". Higher expression levels of gangliosides such as GD3, GD2, GM3, GM1 have been identified in various malignant tumors. Apparently, certain mutations in the multienzyme pathways of ganglioside expression are contributing to physiologically relevant phenomena determining whether cells or tissues behave as "normal" or as "malignant" phenotypes. Even minor deviations in ganglioside expression may cause malignant transformations.

Peter Vollmers and Stephanie Brändlein (Natural antibodies and cancer, New Biotechnology Vol. 25, No. 5, June 2009—Review, Natural IgM antibodies: The orphaned molecules in immune surveillance, Advanced Delivery Reviews; Vol. 58 (2006)) report that most tumor-specific antibodies which they found belonged nearly exclusively to the IgM class. The authors also conclude that tumor immunity seems to be restricted to innate immune mechanisms used by nature, like natural antibodies, which are also most likely considered as excellent therapeutics. Despite major scientific progress in recent years IgM antibodies still remain somewhat neglected and biased by the established antibody researchers community.

European Patent No. 0480440 discloses and claims a monoclonal antibody against melanoma, the antibody comprising an IgM antibody. The present invention may thus be regarded as a useful further development of the invention reported in EP 0480440.

BRIEF DESCRIPTION OF THE INVENTION

The present invention laid down in the independent claims provides for a recombinant human IgM monoclonal antibody that is capable of recognizing different purified ganglioside antigens and that is also capable of specifically binding and killing different malignant tumour or cancer cells via activation of complement effector function while at the same time leaving non-malignant ("normal") cells unaffected.

In one embodiment of the invention the IgM antibody is expressed in its complete pentameric relative IgM isoform by a suitable host cell transfected with genetic material obtained from a healthy human individual.

In accordance with the present invention, malignant tumour cells such as estrogen receptor-negative breast cancer cells, small cell lung cancer cells, melanomas and glioblastomas have been identified as targets for cancer therapy using the present IgM antibodies.

BRIEF DESCRIPTION OF THE FIGURES

FIG. 1A relates to subclone 1G6, FIG. 1B relates to subclone 2E4; abscissa=time period of cultivation in days; left ordinate and diamond symbols=cell concentration; right ordinate and square symbols=viability in %.

FIG. 2A relates to subclone 1G6, FIG. 2B relates to subclone 2E4; abscissa=time period of cultivation in days; left ordinate=sugar concentration in mg/ml: diamonds=glucose, squares=lactose; right ordinate and triangles=product (antibody) concentration in mg/ml.

FIG. 3A relates to subclone 1G6, FIG. 3B relates to subclone 2E4; abscissa=time period of cultivation in days; left ordinate=specific sugar consumption in nanograms per cell per day (ng/cell/d): diamonds=glucose, squares=lactose; right ordinate and triangles=specific antibody expression rate in pg/cell/d.

DESCRIPTION OF THE INVENTION

Figure 1A:
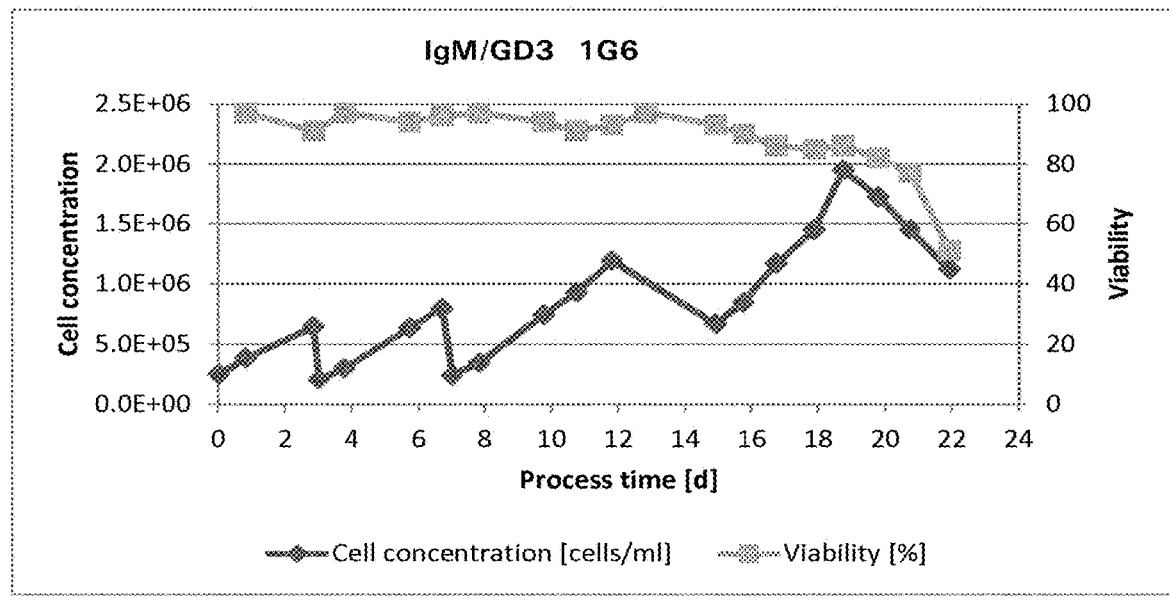
FIGS. 1A and 1B are graphical representations of a viability comparison between subclones 1G6 and 2E4 of an anti-GD3-effective IgM-producing CHO cell line after adaptation to serum-free cell culture medium.

Prior to developing the present invention the cell line disclosed in EP0480440, i.e. deposit no. ECACC 90090703, was obtained and routinely propagated using ex-vivo medium plus 10% FCS, first in tissue culture-bottles and thereafter followed by spinner culture, for comparison purposes. However, the IgM-titer achieved with the state-of-the-art hybridoma was rather low, i.e. in the order of 2-3 ng/ml, although the cell growth was within the typical range for this kind of hetero-hybridomas. In this context it may be mentioned that instability of expression in hetero-hybridomas is an often observed phenomenon and may perhaps also count for the low titers in this comparative cell culture.

Such low expression titers of antibody production are of course not suitable for commercial scale manufacture, neither for diagnostic nor for therapeutic application purposes. It was therefore an object of the present invention to establish a system for recombinant expression of the desired IgM antibody suitable for industrial scale manufacture in order to provide sufficient amounts of IgM as a tool for cancer diagnostics and/or for use as a cancer therapeutic agent.

Comparative Example

EP 0480440 discloses that the IgM antibody secreted by the hybridomas referred to therein is capable of binding to the gangliosides GM3 and GD3. In an attempt to verify said binding specificities a qualified and commercially available anti-ganglioside dot assay was purchased from Generic Assays GmbH, Germany, and was used according to operation procedures described therein. A 10-fold concentrated culture supernatant was used.

A slightly positive signal at the GD3 band was indeed identified. Surprisingly, a signal at the GM3 band position was missing contrary to expections from the disclosure of EP 0480440. A possible explanation therefore could be that the IgM-titer in the concentrated culture supernatant (approx. 20-40 ng/ml) was too low for detectable binding to GM3.

Example 1

Given that GD3-overexpression is repeatedly described in scientific publications for malignant cells such as melanomas it was decided to focus on the recombinant expression of the antibody of interest. The gene construct used for this purpose was preliminarily named PolrecCHOIgM/GD3. The heavy and light chain cDNAs of the hybridoma producing an IgM binding to GD3 have then been isolated using established techniques of gene isolation and transfection to CHO host cell lines. The heavy-chain and light-chain polypeptide sequences of the variable regions are listed hereinafter. Codon optimization for expression in different host cell species enabled by various state of the art techniques has been carried out for various embodiments of the invention but is not specifically disclosed herein.

SEQ ID NO:1: PolrecCHOIgM/GD3 heavy chain variable region of mature protein QVQLVQSGAEMKKPGASVKVSCKASGYTFSSFAMHWVRQAPGQRLEWMGWINAGNGNTKYSQKFQGRLTITRDTSASTAYMDLSSLRSEDTAVYYCARNLNYYDILTGL DAFDIWGQGTMVTVSSG SEQ ID NO:2: PolrecCHOIgM/GD3 light chain variable region of mature protein DIVMTQSPDSLAVSLGERATINCKSSQSVLYSSNKKNYLAWYQQKPGQPPKLLIYWASTRESGVPDRFTGSGSGTDFTLTISSLQAEDVAVYYCQQYYSTPLTFGPGTKVDIK The polypeptide sequences of the constant regions of heavy and light chains are reactive with polyclonal antisera against mu and kappa chains respectively.

In order to establish recombinant CHO cell clones expressing the anti-GD3 IgM antibody a rather complex cloning and selection program was applied comprising a series of state-of-the-art procedures that have been optimized to a certain extent and standardized according to the present needs. The cloning and selection program comprised the following procedural steps:

(i) Identification, isolation and sequencing of the genes encoding the IgM target molecule from the original hybridoma referred to in EP 0480440, i.e. identified by their deposit numbers ECACC 90090701 or ECACC 90090703;

(ii) Codon-optimization for expression in the host cell-line, in the present case a CHO dhfr⁻ cell line (dhfr⁻=dihydrofolate reductase deficient);

(iii) Construction of vectors, transfection and selection of positive CHO-clones;

(iv) Several rounds of subcloning and genedose amplification via MTX-resistance selection;

(v) Cultivation of the most promising subclones with respect to proof of stability of IgM expression and proliferation;

(vi) Adaptation and selection of subclones in suitable protein-free media with continued monitoring of both stability of IgM-expression and acceptable proliferation activity;

(vii) Adaptation and selection of subclones that firmly and stably express IgM and subsequent propagation of said subclones in small-scale stirred tank bioreactor environments as suitable and required for scale-up for industrial manufacture.

This research program has been applied for establishing and selecting a recombinant CHO-clone having the potential for industrial scale manufacture at a proper quality of a human recombinant IgM antibody having GD3 binding specificity, hereinafter named "IgM/GD3". In figures FIG. 1A through FIG. 3B some important parameters of two different IgM/GD3 expressing subclones are compared as determined in experiments performed in small-scale stirred tank reactors (Sixfors) operated at a working volume of 500 ml.

Figure 1B:
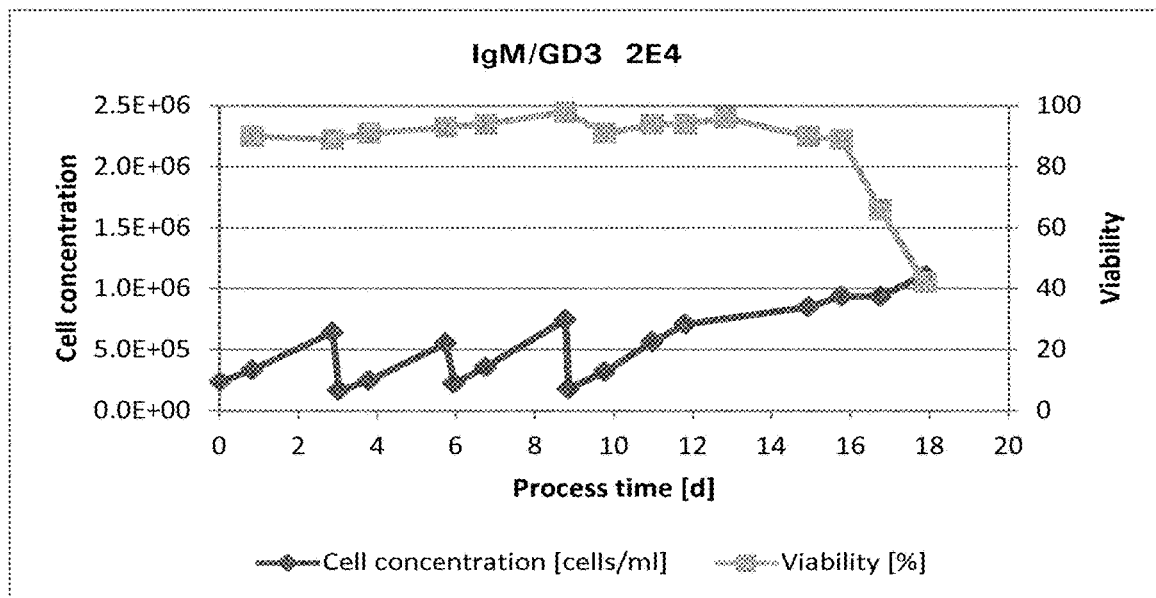
Figure 2A:
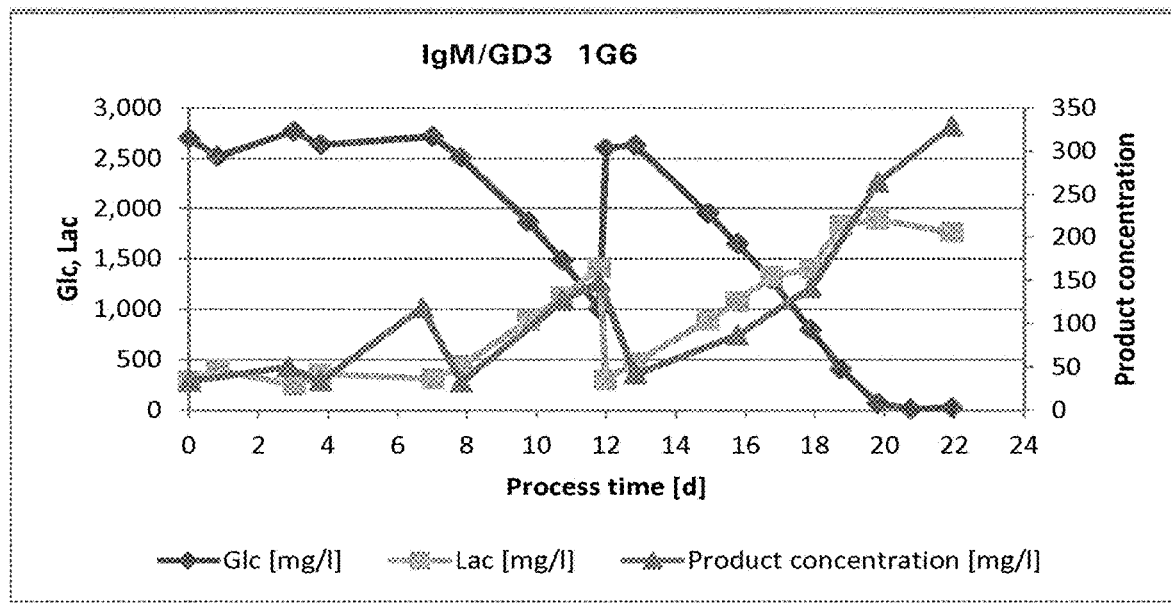
FIGS. 2A and 2B are graphical representations of a comparison in total product yield between subclones 1G6 and 2E4 of an anti-GD3-effective IgM-producing CHO cell line after adaptation to serum-free cell culture medium.
Figure 2B:
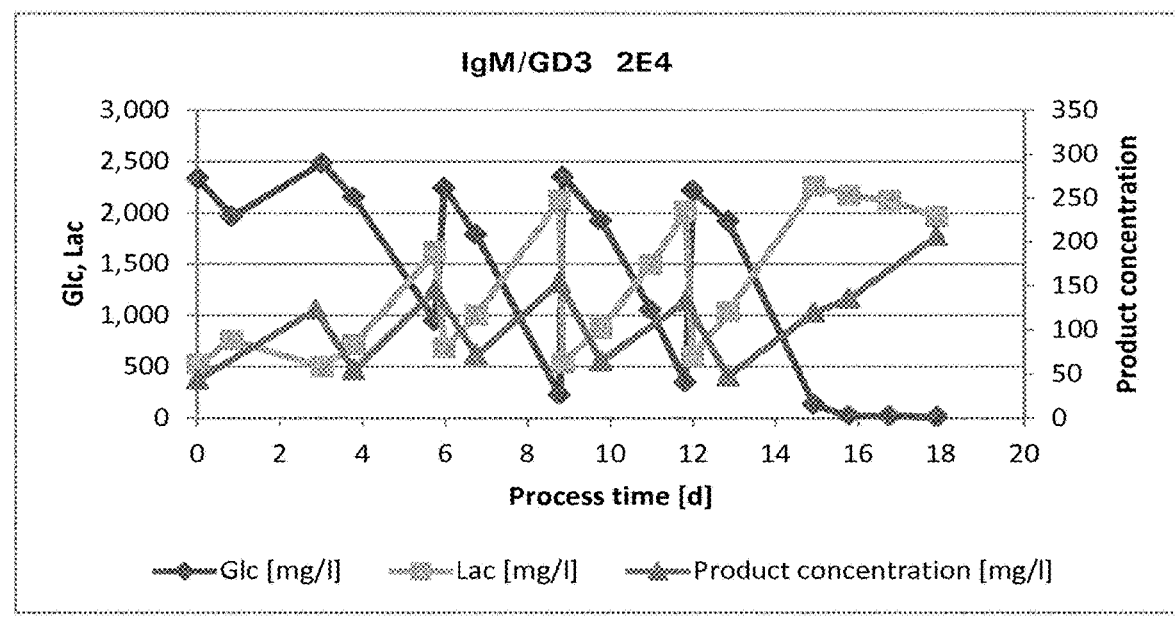

As can be taken from FIG. 1A and FIG. 1B the subclone "1G6" in the stirred tank mini-reactor exhibited a superior robustness with respect to proliferation in the protein-free medium (batch cultures were compared) while subclone "2E4" seemed to be rather sensitive in that physico/chemical environment, resulting in a sharp decrease in viability after 16 days of cultivation whereas subclone 1G6 maintained approx. 80% viability for 5 more days, i.e for 21 days.

Figure 3A:
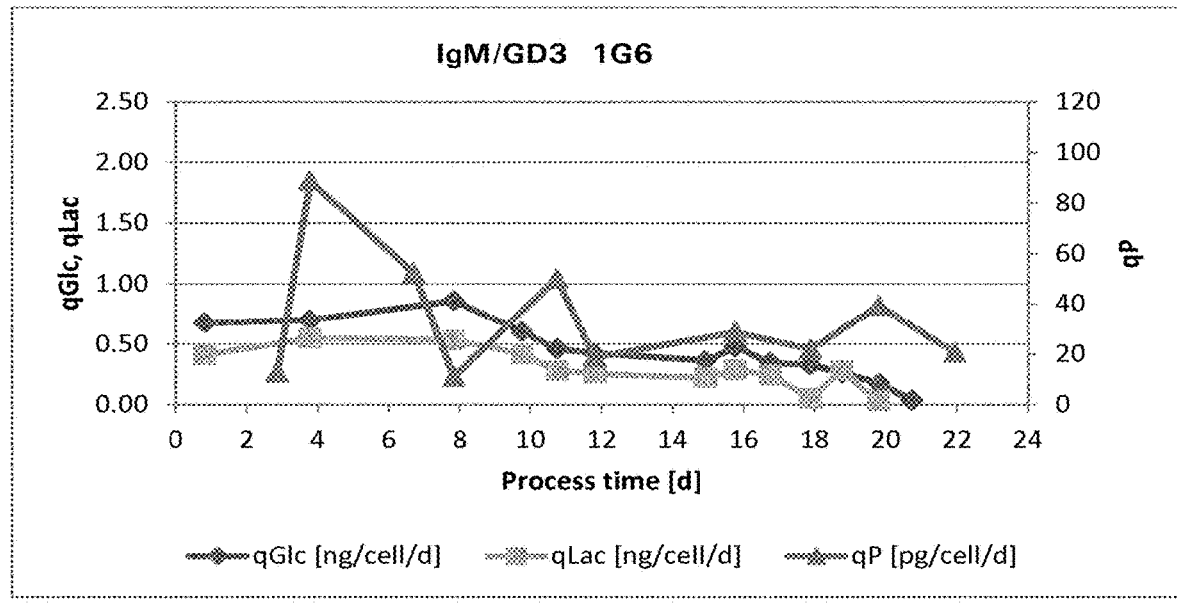
FIGS. 3A and 3B are graphical representations of a comparison in specific expression rates between subclones 1G6 and 2E4 of an anti-GD3-effective IgM producing CHO cell line after adaptation to serum-free cell culture medium.
Figure 3B:
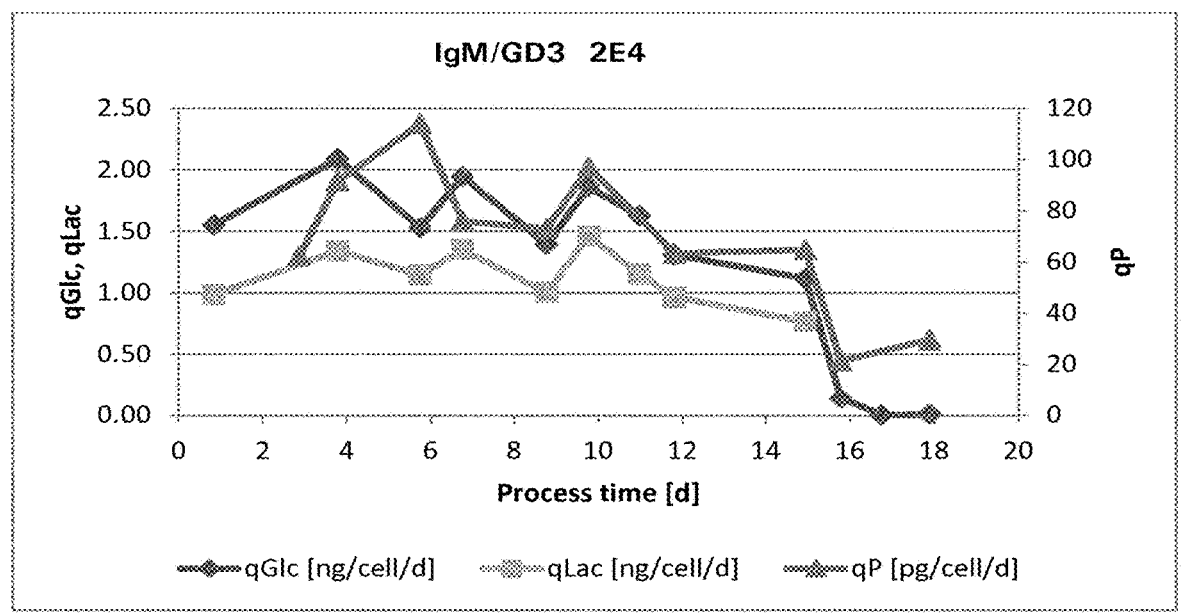

Also, grown under identical culturing conditions the IgM-titers of subclone 1G6 (see FIG. 2A and FIG. 2B) were significantly higher (i.e. 325 mg/l after 22 days of culturing) than the IgM-titers yielded with subclone 2E4 (i.e. 200 mg/l after 18 days of culturing), although the specific IgM expression rate qP of subclone 2E4 was significantly higher, i.e. prevailingly at or above approximately 60 pg/cell/d, relative to the specific product expression rate qP of subclone 1G6, which remained typically in a range of about 30 pg/cell/d (see FIG. 3A and FIG. 3B).

Although there is certainly quite some potential for further optimization it is evident from the experimental results that the recombinant expression of the IgM/GD3 antibody in CHO host cells is several orders of magnitude more efficient than IgM/GD3 production using one of the original, i.e. state-of-the-art, hybridoma cell lines referred to in EP 0480440. The recombinant expression procedure according to the present invention thus allows for industrial scale production of the IgM/GD3 antibody for both diagnostic and therapeutic applications.

IgM antibodies are representing extremely large and complex glycoprotein structures which in the native situation in vivo are correctly expressed and secreted as pentameric isoforms only by certain peripheral B-lymphocytic cells. According to the present inventors' experience it is not obviously derivable nor predictable from prior art knowledge whether a genetically engineered host cell will be able to recombinantly express complete pentameric IgM-isoforms. Most often times various isoforms are secreted from a recombinant host cell resulting in a mixture of hexamer, pentamer structures and a series of lower molecular weight IgM-fragments. The underlying factors or conditions causing posttranslational fragmentation or incomplete synthesis are still unknown so far (see e.g. S. Wolbank et al., J. of Virology, Vol. 77(2003), p. 4095-4103).

It is therefore stressed in this context that present subclone 1G6 is secreting the IgM/GD3 antibody as a nearly 100% pentameric isoform. Only traces of fragments in the 60 kilodalton range are detected by IgM-SDS PAGE (Novex System; data not shown herein) which traces are also found in the IgM reference sample derived from human serum.

Also, while the IgM reference sample derived from human serum contained a significant amount of hexameric IgM isoforms such hexameric isoforms were not detected in the recombinant IgM/GD3 fraction of the manufacturing process of the present invention. It can therefore be concluded that the present recombinant CHO host cell expresses the human IgM almost quantitatively as a pentamer. In the light of prior art knowledge this is a rather rare and surprising finding (see, for example, Karola Vorauer-Uhl et al.: "IgM characterization directly performed in crude culture supernatants by a new simple electrophoretic method". Journal of Immunobiological Methods 359 (2010, 21-27))

Example 2

Figure 4:
FIG. 4 discloses the results of a Generic Assays immuno-dot-blot test of a cell culture supernatant at different dilutions obtained after cultivation of the present IgM producing CHO cell line in a mini-fermentor (Sixfors, working volume 500 ml). Rows 01 through 03 relate to the positive control sample applied at volumes of 10, 50 and 100 uL (uL=microliter); rows 15 through 20 relate to supernatant samples of two different batches, tested at dilutions of 1:6, 1:21 and 1:101, respectively.

In order to confirm the binding specificity of the present human recombinant IgM/GD3 antibody the GA Generics Assay Test-Kit for immuno-dot-blot testing was applied again. The test results are shown in FIG. 4.

Figure 5:
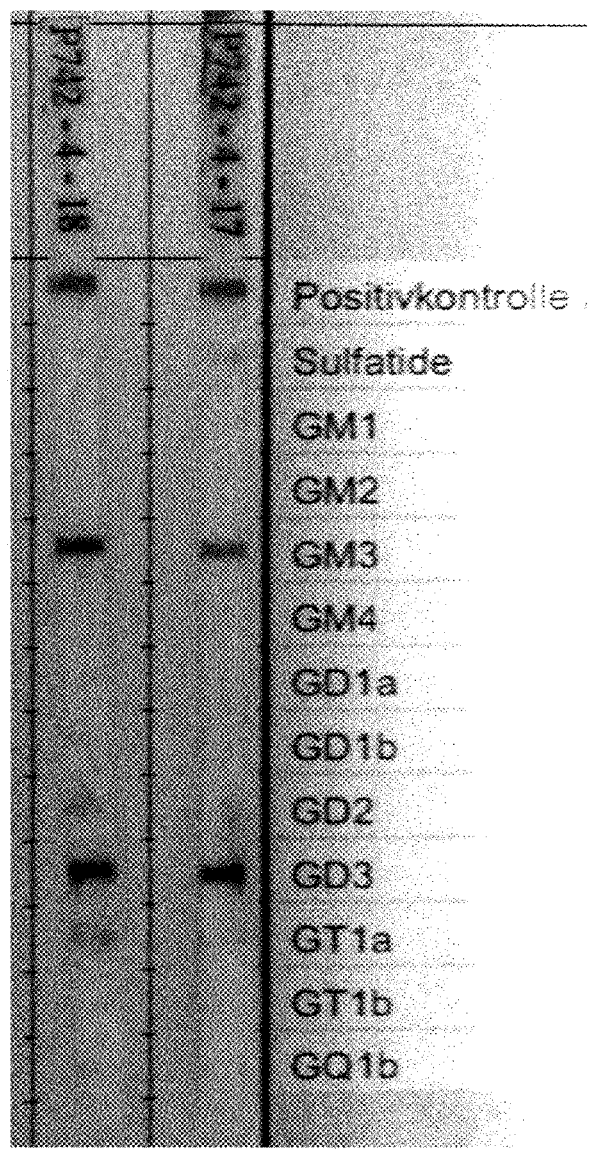
FIG. 5 discloses the results of a Generic Assays immuno-dot-blot test of purified, i.e. almost 100% pentameric, anti-GD3 IgM antibody at a concentration of approx. 50 ug/ml). Left lane=purified anti-GD3 IgM antibody (=IgM/GD3); right lane=culture supernatant comprising IgM/GD3 at a concentration of approx. 50 ug/ml (ug=microgram).

Anti-ganglioside dot-blot-test results of recombinant "IgM/GD3": Culture supernatants from the 500 ml minifermenter (Sixfors) obtained with serum-free nutrient medium have been tested in various dilutions (1:6; 1:21; 1:101; see FIG. 4). In all dilutions of the culture supernatant a clearly positive binding to GD3 is visible on the test strip. Later, when purified recombinant IgM/GD3 was available the immuno-dot-blot test was repeated with purified, i.e. 100% pentameric IgM/GD3 antibody. As can be seen in FIG. 5, in addition to its binding capacity with GD3 (see FIG. 5, right lane) purified IgM/GD3 antibody also yielded a clearly positive reaction with GM3 (see FIG. 5, left lane). Moreover, there is also visible some weak binding with GT1a, GD2 and GQ 1 b (the latter better visible in the original test read-out). Surprisingly, these additional binding characteristics are not seen under the experimental conditions represented in FIG. 4.

There is no scientific basis for explaining the slightly different binding results obtained with the crude culture supernatant and its dilutions (FIG. 4) on one hand and with purified IgM/GD3 antibody (FIG. 5) on the other hand. It was therefore assumed that perhaps variations in quality of the Generic Assays ganglioside immuno-dot-blot test kits could have accounted for these differing test results. Accordingly, only purified gangliosides, as far as available, were used for further testing in order to clarify the binding specificities of recombinant IgM/GD3 antibody, which apparently could also be named IgM/GD3/GM3 antibody due to its additional GM3 binding specificity. In any case, antibody IgM/GD3 turned out to be also cross-reactive with additional ganglioside antigens or epitopes, respectively, at least to some extent.

The clarification of cross-reactivities is of particular interest since according to scientific literature natural IgMs, in contrast to antibodies generated by humoral immune response upon infection or vaccination, are generally characterized by limited specificity and rather low binding affinity to their respective epitopes as compared to the binding affinities of maturated IgGs. Natural IgMs generally show cross-reactivities in binding to different subtypes of antigens or epitopes within chemically related but not identical antigen structures. It is hypothesized that a certain cross-reactivity with generally lower binding affinity is an inherent function enabling their role in the general surveillance of the immune response.

Example 3

A series of additional binding tests of the recombinant IgM/GD3 monoclonal antibody with purified ganglioside antigens available on the market have been performed in immunochemical ELISA-test formats. All purified ganglioside antigens have been purchased from Calbiochem/Merck Biosciences.

The standard ELISA test format applied was as follows:
96-well plates from Nunc or Corning were used which typically have comparable quality with respect to lot-to-lot consistency. For precoating the plates with ganglioside antigens generally concentrations of 500 ng/ml or 1000 ng/ml have been optimized to improve assay quality. Routinely, the test-specific antibodies are subject to biotinylation using biotinylation kits from Amersham according to the standard operation procedures recommended by the supplier. Streptavidin peroxidase conjugate is used for OD read-out. Generally, this procedure results in highly sensitive and consistent test formats whereas when using the Generic Assays anti-ganglioside immuno-dot-blot tests differing results were observed, as pointed out above (see also FIG. 4 and FIG. 5). This test format is designed for testing using biotinylated IgM molecules. Therefore native, i.e. non-biotinylated IgMs were tested in a slightly modified ELISA test format using anti-kappa-chain antibody alkaline phosphatase conjugate for OD read-out in order to be able to compare native IgMs with biotinylated IgMs. Both ELISA test formats have at first been compared with respect to specificity and sensitivity of binding to ganglioside antigen GD3, since positive reaction of the present recombinant IgM with GD3 was already established.

Both ELISA test formats confirmed positive binding of the IgM antibody to GD3 in accordance with the Generic Assays anti-ganglioside immuno-dot-blot (data not shown herein). There is apparently no interference of biotinylation with respect to binding specifity. As expected, the ELISA test format using biotinylated IgM and streptavidin peroxidase OD read-out was slightly more sensitive than the one using the native IgM anti-kappa chain alkaline phosphatase OD read-out. As there was no indication that the biotinylation would interfere with binding specificity the screening for binding specificities of the recombinant IgM antibody was continued using the standard ELISA test format with biotinylated IgM and additional purified ganglioside epitopes.

The test results achieved with GM3 (data not shown herein) confirm that there is a clear positive binding specificity of the present IgM antibody for GM3, in accordance with the test results observed with the Generic Assays blots. The sensitivity of binding to GM3 is comparable to the sensitivity of binding to GD3 and is in the range of lower than 7 ng/ml.

Surprisingly, further screening with respect to binding to purified ganglioside antigens purchased from Calbiochem/ Merck Biosciences led to unexpected results, namely to unveiling a positive binding of the recombinant IgM pentamer to GM1 and GD2 ganglioside antigens. In order to confirm or exclude the first screening observations different biotinylated IgM concentrations were applied in the ELISA test format. The results are shown below in Table 1 (GM1) and Table 2 (GD2).

Clear positive, consistent and dilutable binding reactions to the ganglioside antigens GM1 and GD2 were obtained which are in a comparable order of sensitivity as compared to GD3 and GM3 binding, respectively. A minor cross-reactivity with GD2 was previously visible from FIG. 5 too, but a cross-reactivity with GM1 was not visible at all from the results represented by FIG. 5.

The recombinant "1G6" CHO cell line producing the present IgM/GD3 antibodies was deposited at the Health Protection Agency Culture Collection, Microbiology Services Division, Porton Down, UK, on 29 Jun. 2011, pursuant to the Budapest Treaty of 1977, under HPA Culture Collections Reference Number: Q9165, and Accession Number 11062901. Hereinafter, it will be referred to as CHO cell line "IgM/Q9165".

TABLE 1

Binding to GM1 ganglioside at different concentrations of biotinylated IgM

BIOLISE
Protocol description

| Name: | NONAME.PRT | | MODIFIED |
| --- | --- | --- | --- |
| Reader: | SPECTRA | Wavelength: | 492 7 620 nm |
| Lag time: | 0 s | Mode: | Normal |
| Shaking: | No | | |

Assay Description

| Data Name: | D:\NTFSDATA\11494A.PLA | | |
| --- | --- | --- | --- |
| Reading Type: | Reader | | |
| Reading Date: | 22/11/2011-13:48:17 | Report Date: | 29/10/2012-15:13:37 |
| Prompt #1: | Precoating GM1 [1000 ng/ml] | Prompt #4: | 10/10/2012 |
| Prompt #2: | biotinilated IgM | Prompt #5: | |
| Prompt #3: | different internal lots | Prompt #6: | |
| Comments: | blanks row 1, 5 and 9; different concentrations of biotinilated IgM[H2, 3, 4, 2000 ng/ml; [H 6, 7, 8, 200 ng/ml; and [H 10, 11, 12, 20 ng/ml, 1:2 dilutions from H to A and readout with streptavidin POD conjugate. Lot from ganglioside, D00091608, from Calbiochem | | |

Delta OD

| | 1 | 2 | 3 | 4 | 5 | 6 | 7 | 8 | 9 | 10 | 11 | 12 |
| --- | --- | --- | --- | --- | --- | --- | --- | --- | --- | --- | --- | --- |
| A | 0.002 | 0.103 | 0.074 | 0.061 | 0.023 | 0.088 | 0.044 | 0.051 | 0.020 | 0.025 | 0.024 | 0.042 |
| B | 0.002 | 0.115 | 0.109 | 0.085 | 0.021 | 0.052 | 0.055 | 0.057 | 0.018 | 0.025 | 0.029 | 0.074 |
| C | 0.002 | 0.177 | 0.163 | 0.129 | 0.021 | 0.077 | 0.081 | 0.081 | 0.018 | 0.031 | 0.034 | 0.059 |
| D | 0.003 | 0.268 | 0.288 | 0.235 | 0.023 | 0.123 | 0.138 | 0.140 | 0.019 | 0.046 | 0.042 | 0.056 |
| E | 0.003 | 0.427 | 0.462 | 0.390 | 0.021 | 0.209 | 0.213 | 0.208 | 0.028 | 0.064 | 0.069 | 0.138 |
| F | 0.010 | 0.827 | 0.802 | 0.650 | 0.032 | 0.361 | 0.366 | 0.358 | 0.021 | 0.117 | 0.121 | 0.133 |
| G | 0.012 | 1.238 | 1.300 | 1.057 | 0.034 | 0.608 | 0.626 | 0.605 | 0.024 | 0.174 | 0.183 | 0.194 |
| H | 0.016 | 1.905 | 1.985 | 1.678 | 0.037 | 1.022 | 1.031 | 1.016 | 0.028 | 0.299 | 0.304 | 0.333 |

TABLE 2

Binding to GD2 ganglioside at different concentrations of biotinilated IgM

BIOLISE
Protocol description

| | | | |
|---|---|---|---|
| Name: | NONAME.PRT | | MODIFIED |
| Reader: | SPECTRA | Wavelength: | 492 7 620 nm |
| Lag time: | 0 s | Mode: | Normal |
| Shaking: | No | | |

Assay Description

| | | | |
|---|---|---|---|
| Data Name: | D:\NTFSDATA\11228B.PLA | | |
| Reading Type: | Reader | | |
| Reading Date: | | Report Date: | 11/10/2012-13:08:49 |
| Prompt #1: | precoating GD2 gangliosid | Prompt #4: | 10/10/2012 |
| Prompt #2: | wir 1000n ng/ml, biotinilated | Prompt #5: | |
| Prompt #3: | IgM internal lot, 020511-A | Prompt #6: | |
| Comments: | blanks row 1, 5 and 9; rows 2-4 IgM biotinilated, lot: 20511-A [2000 ng/ml and rows 6-8 IgM, biotinilated, lot: 260511-A [200 ng/ml and rows 10-12 igM biotinilated, lot: 80611-A with 20 ng/ml and 1:2 dilutions H to A; readout with streptavidin POD conjugate | | |

Delta OD

| | 1 | 2 | 3 | 4 | 5 | 6 | 7 | 8 | 9 | 10 | 11 | 12 |
|---|---|---|---|---|---|---|---|---|---|---|---|---|
| A | 0.072 | 0.106 | 0.084 | 0.072 | 0.026 | 0.047 | 0.148 | 0.015 | 0.022 | 0.025 | 0.029 | 0.044 |
| B | 0.080 | 0.138 | 0.126 | 0.098 | 0.028 | 0.060 | 0.073 | 0.059 | 0.021 | 0.027 | 0.032 | 0.041 |
| C | 0.095 | 0.195 | 0.198 | 0.156 | 0.036 | 0.102 | 0.093 | 0.089 | 0.022 | 0.034 | 0.036 | 0.055 |
| D | 0.070 | 0.298 | 0.322 | 0.270 | 0.030 | 0.153 | 0.151 | 0.149 | 0.025 | 0.047 | 0.047 | 0.066 |
| E | 0.074 | 0.492 | 0.520 | 0.408 | 0.031 | 0.235 | 0.240 | 0.234 | 0.023 | 0.072 | 0.068 | 0.089 |
| F | 0.103 | 0.766 | 0.831 | 0.716 | 0.028 | 0.392 | 0.397 | 0.438 | 0.023 | 0.112 | 0.112 | 0.135 |
| G | 0.092 | 1.305 | 1.361 | 1.144 | 0.031 | 0.672 | 0.695 | 0.655 | 0.023 | 0.183 | 0.184 | 0.197 |
| H | 0.105 | 1.990 | 2.131 | 1.823 | 0.033 | 1.096 | 1.095 | 1.101 | 0.026 | 0.315 | 0.313 | 0.330 |

Example 3

Basically any therapeutic or diagnostic potential of an antibody is determined by its potency to differentiate between desired and undesired binding targets, e.g. in the best case to exhibit reliable binding to a broad spectrum of malignant cells and no binding to normal phenotypes at all. Accordingly, it was decided to select some primary (normal) cells and some well characterized malignant cell lines isolated from different tumor tissues in order to investigate the binding patterns of present IgM/GD3 antibody as expressed by CHO cell line IgM/Q9165. Since we did not detect any differences in ganglioside binding patterns between the native IgM/GD3 antibody and its biotinylated derivative it was decided to use the biotinylated antibody for immunoimaging microscopy. The different cells investigated and the results of immunoimaging are summarized in Table 3.

TABLE 3

Immunoimaging microscopy of human cells after contacting with biotinylated IgM/GD3.

| Cell Name | Cell Type | Origin | Results of binding study |
|---|---|---|---|
| MeWo; ATCC no. HTB-65 | Adherent fibroblast | human skin/malignant melanoma | positive |
| NCI-H69; ATCC no. HTB-119 | multicell aggregates | human lung/small cell lung cancer, SCLC | positive |
| MDA-MB-231; ATCC no. HTB-26 | adherent epithelial | human metastatic breast cancer | positive |
| HTB14 | adherent fepithelial | human glioblastoma | positive |
| ERL1690 | adherent fibroblast | human glioblastoma | positive |
| huVEC | adherent endothelial | human umbilical vein endothelium | negative |
| HDF5 IAM* | adherent fibroblastoid | human lung primary normal | negative |
| RPTEC IAM* | adherent epithelial | Human kidney immortal. normal | negative |

*IAM—Institute of Applied Microbiology, Vienna Institute of Biotechnology

All cells were seeded into 8-well-chamber slides (μ-well ibi Treat, Microscopy Chambers) in sub-cultivation ratios and growth media according to the recommendations of the particular cell culture collections from which they were purchased. According to the recommended protocols the cells should be still growing after an incubation time of 1 to 2 days and cell density should not be too high in order to allow for suitable immuno imaging. Most of the cell lines depicted in Table 3 were growing strongly adherent which facilitated washing and fixation steps without cell losses, except for both SCLC-cell lines (cor L88 and HTB 119) which only weakly adhered resulting in more sophisticated washing and fixation steps and some cell losses.

After incubation for a maximum of 2 days cell fixation was done as follows:

a) cells have been treated twice with washing buffer (phosphate buffered saline (PBS) containing 10% fetal calf serum);
b) after the washing step the cells have been covered with 3% of paraformaldehyde solution in PBS for 15 minutes at room temperature, for fixation;
c) after fixation the paraformaldehyde solution has been removed and cells have been washed twice again. Wells have then been covered with 10% FCS in PBS plus 0.3 molar glycine for 30 minutes at room temperature in order to saturate or block unspecific binding reactions (e.g. free aldehyde groups originating from the fixation with paraformaldehyde);
d) thereafter the blocking solution has been discarded and the fixed cell layer has been incubated in parallel with either biotinylated IgM/GD3 antibody (working concentration 10 ng/ml) as positive control or with 10% FCS in OBS as negative control for 1 hour at room temperature;
e) thereafter the incubation solutions have been decanted, the wells rinsed twice with washing solution followed by incubation with Qdot 525 streptavidin conjugate (working concentration 20 ng/ml) for approx. 1 hour;
f) in most experiments counter-staining of the cell nucleus with DAPI has been applied. In such procedures the cells have again been washed twice and thereafter incubated with DAPI solution (200 nl DAPI dissolved in 10 ml PBS) for 15 minutes;
g) for microscopic immuno imaging the wells have been rinsed again with PBS and then covered with PBS for analysis.

Binding of Qdot streptavidin to biotinylated IgM/GD3 resulted in green light emission signalling positive binding, which green light emission was automatically measured and corrected against unspecific background by the software of the microscope. Staining or counter staining with DAPI lead to blue light emission. Generally, microscopic magnification was 600 times.

From the results of immuno imaging it was concluded that IgM/GD3 antibody has indeed the potential to discriminate in binding between malignant and non-malignant, i.e. "normal", human eukaryotic cells.

Example 4: Investigation of Effector Functions Triggered by IgM/GD3 Antibody

According to text book teachings of modern immune biology (see e.g. JANEWAY's IMMUNO BIOLOGY, 5$^{th}$ edition, Kenneth Marghy, Garland Science) IgM antibodies are expected to induce effector functions such as apoptosis and activation of the complement cascade leading to killing of the respective target cells to which they bind. It is still unclear whether they are also able to activate ADCCs (antibody dependend cytotoxic cells) as there are contradictory expert opinions which are difficult to verify in standard animal models. At present, reliable results can only be expected and obtained from clinical trials with human volunteers afflicted with cancer.

Nevertheless, in order to test the potency of the IgM/GD3 pentameric antibody to kill certain target cells via activation of the human complement cascade a complex in vitro test system simulating an even more complex in vivo situation was established comprising the following procedural steps:

a) Culturing of target cells was done in a cell culture medium as recommended by the respective cell culture collection from which the cell lines have been obtained and supplemented with 20% of heat inactivated normal human serum (hiNHS). The heat inactivation (56° C. for 1 hour) destroys or inactivates at least some of the proteins involved in the activation of the complement cascade. Supplementation with hiNHS was thus used as a reference standard marker for 100% cell propagation in a human serum environment.

b) Supplementation of cell culture medium with 20% of normal human serum (NHS), i.e. without heat-inactivation, in replacement of hiNHS, as a source of human complement proteins (of which approximately 30 different proteins have been identified in the prior art). NHS was thus intended to represent the composition of human blood from which all cellular components have been removed while all soluble constituents have been left essentially unchanged.

c) Addition of the IgM/GD3 antibody at different concentrations to the target cell culture supplemented with NHS and determination of the percentage of surviving cells as compared to the cell cultures supplemented with hiNHS or NHS, respectively, but without addition of the IgM/GD3 antibody. Antibody concentrations tested varied in a range of from 1 ug/ml to 100 ug/ml. Specific antibody concentrations selected comprised 1, 2, 4, 10, 20, 40 and 100 ug/ml (see FIGS. 6-8)

Figure 6:
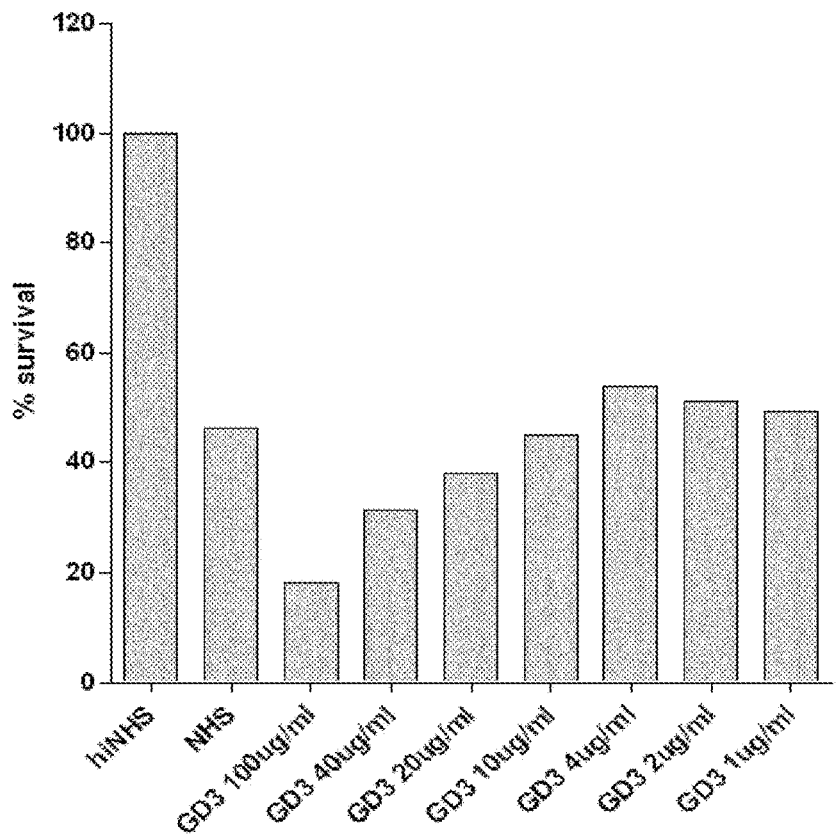
FIG. 6 is a graphical representation of the experimental results obtained from in vitro activation of complement by the present IgM/GD3 antibody in the presence of 20% of natural, i.e. non-heat-inactivated, human serum (NHS) as the source of compliment. Ordinate=cell survival in %, 100% being the viable cell count in cell culture medium supplemented with heat inactivated NHS (hiNHS); abscissa=hiNHS and NHS controls without antibody, and various concentrations in the range of from 1 to 100 ug/ml of anti-GD3 IgM antibody added to the cell culture of CRL-1690 cells.
Figure 7:
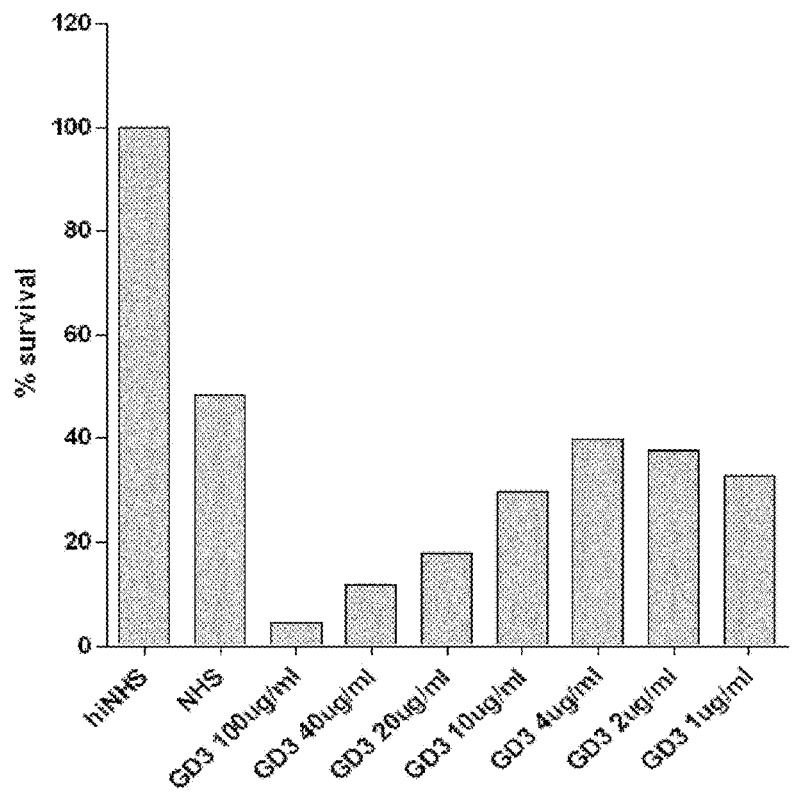
FIG. 7 is a graphical representation of experimental results analogous to the ones set out in FIG. 6 and obtained under analogous experimental conditions, however exemplified with COR-L88 cells.
Figure 8:
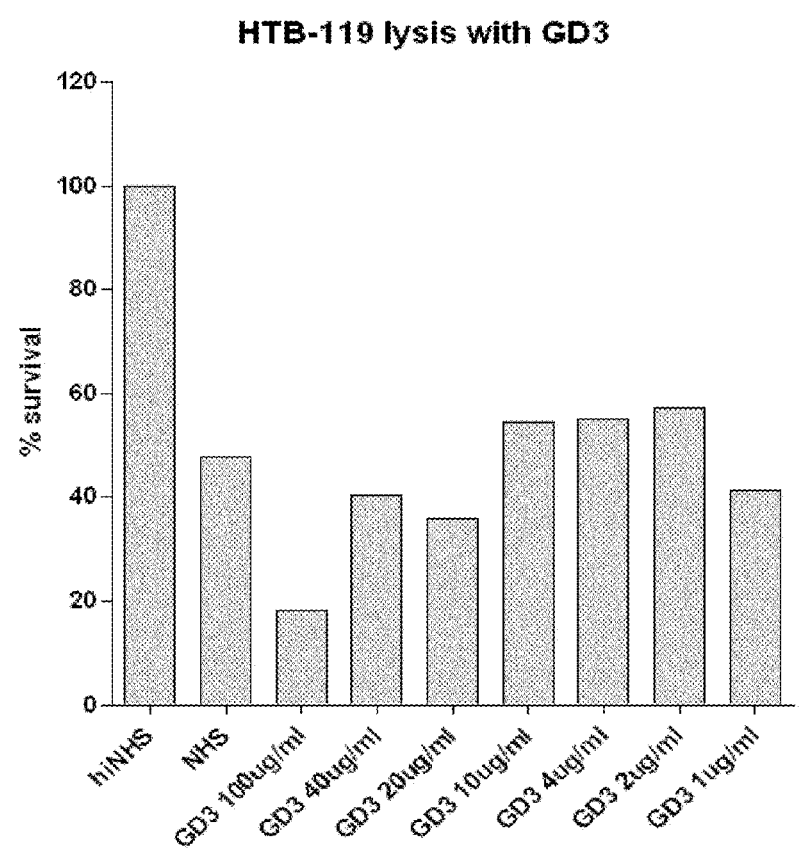
FIG. 8 is a graphical representation of experimental results analogous to the ones set out in FIGS. 6 and 7 obtained under analogous experimental conditions, however exemplified with HTB-119 cells.

In FIGS. 6 through 8 the results of an in vitro test series with three different target cell lines are shown (for identification of target cells see Table 3 above). It can be taken therefrom that supplementation of the cell culture medium by 20% of NHS as a source of complement was effective in causing the lysis of some target cells depending on the concentration of the anti-GD3 antibody IgM/GD3 added to the respective cell cultures.

The fact that replacement of hiNHS by NHS in the absence of antibody also exhibits some cell lysis or growth inhibition is not surprising and is a well-known though not yet well understood phenomenon.

Anyway, from the results achieved by immunoimaging of "malignant" and "normal" cells summarized in Table 3 above as well as from the results of in vitro testing of complement activation it is concluded that the present antibody IgM/GD3 is well suited for both diagnostic and therapeutic use, e.g. for diagnostic formulations to detect cancer cells in biopsies or blood samples, as well as for therapeutic applications to treat various cancers. The present invention therefore also relates to the use of the present anti-GD3 IgM antibody as a diagnostic tool in the course of in vitro or in vivo cancer diagnostics of human individuals. The invention further relates to the use of the present anti-GD3 IgM antibody as an active ingredient in a pharmaceutical composition or medicament for therapeutical application in the treatment of cancer.

While the present invention has been exemplified with human recombinant "1G6" IgM/GD3 antibody obtainable by CHO dhfr cell line IgM/Q9165, deposited at the Health Protection Agency Culture Collection, Microbiology Services Division, Porton Down, UK, on 29 Jun. 2011, pursuant to the Budapest Treaty of 1977, under HPA Culture Collections Reference Number: Q9165 and Accession Number 11062901, it is understood that the present invention also encompasses other anti-GD3 IgM antibodies that have essentially the same binding characteristics as hereinbefore disclosed of deposited antibody IgM/GD3 and/or that compete with said antibody IgM/GD3 for binding to specific epitopes and which other antibodies have been obtained via other routes.

For example, the present invention also relates to IgM/GD3-like antibodies that have been genetically or chemically modified, particularly at the light and heavy chain variable regions, by using state of the art techniques known to the skilled artisan such as modification, deletion, insertion or substitution of genetic information leading to modified nucleotide and/or amino acd sequences as compared to present sequences SEQ ID NO: 1 and SEQ ID NO: 2, to the extent that the resulting IgM antibodies typically share at least 90%, preferably at least 95% sequence homology of their respective heavy and/or light chain variable regions with either or both of the amino acid sequences SEQ ID NO: 1 and SEQ ID NO: 2, and in addition share essentially the same specific binding characteristics with the presently disclosed and claimed CHO antibody IgM/GD3. The present invention also relates to the use of the present IgM/G3 antibody as a screening tool in the development of anti-anti-idiotype antibodies. More specifically, in one embodiment the invention relates to anti-anti-idiotype antibodies obtained by using present antibody IgM/GD3 or fragments thereof as screening tools in a first procedural step in a screening setup for the detection of antibodies that compete with IgM/GD3 for specific binding to one or more of the ganglioside epitopes mentioned hereinbefore. Preferably, such anti-anti-idiotype IgM antibodies in their heavy and/or light chain variable regions share at least 90%, and more preferably at least 95% of sequence homology with either or both of the corresponding idiotype peptide sequences SEQ ID NO: 1 and SEQ ID NO: 2.

What is claimed is:

1. A recombinant human monoclonal IgM antibody which comprises in its heavy chain variable region a polypeptide amino acid sequence SEQ ID NO:1 and in its light chain variable region a polypeptide amino acid sequence SEQ ID NO:2;
the IgM antibody further comprising the following characteristics:
  a) capability of oligospecific binding to purified ganglioside epitopes GD3, GM3, GD2 and GM1; and
  b) capability of specific binding to malignant cancer cells selected from the group consisting of melanoma cells, small cell lung cancer cells, glioblastoma cells, estrogen receptor-negative metastatic breast cancer cells,
said IgM antibody being secreted by a CHO cell line deposited under accession number 11062901 at the Health Protection Agency Culture Collection, Microbiology Services Division, Porton Down, UK.

2. The IgM antibody of claim 1, which is capable of binding said malignant target cells and killing them via complement activation in a dose-dependent manner.

3. The IgM antibody of claim 1, which does not bind to non-malignant normal cells of the human body selected from the group consisting of human umbilical vein endothelial cells, human lung primary cells, and immortalized human kidney cells.

4. The IgM antibody of claim 1, which is in pentameric form.

5. The IgM antibody of claim 1, used as a diagnostic tool in cancer diagnostics.

6. The IgM antibody of claim 1, used in the therapeutic treatment of cancer.

7. A method of cancer diagnostics comprising contacting malignant target cells in vitro or in vivo in the presence of normal, non-heat inactivated, human blood serum with the IgM antibody according to claim 1, and evaluating binding of said antibody to said target cells and/or evaluating IgM-triggered lysis of said target cells by ex vivo methods.

8. The cancer diagnostic method of claim 7, wherein evaluation of target cell binding and/or target cell lysis comprises immuno imaging methods.

9. A method of therapeutic treatment of cancer in an individual in need of such treatment, comprising administering to a said individual afflicted with cancer an anti-cancer effective dose of the IgM antibody defined in claim 1.

* * * * *